(12) United States Patent
Gazenko (10) Patent No.: US 8,663,909 B2
(45) Date of Patent: Mar. 4, 2014

(54) DEVICE FOR RAPID DETECTION AND IDENTIFICATION OF SINGLE MICROORGANISMS WITHOUT PRELIMINARY GROWTH

(75) Inventor: Sergey Gazenko, Mason, OH (US)

(73) Assignee: Nanologix, Inc., Hubbard, OH (US)

( * ) Notice: Subject to any disclaimer, the term of this patent is extended or adjusted under 35 U.S.C. 154(b) by 693 days.

(21) Appl. No.: 11/109,857

(22) Filed: Apr. 20, 2005

(65) Prior Publication Data

US 2005/0221403 A1 Oct. 6, 2005

Related U.S. Application Data

(63) Continuation of application No. 10/141,677, filed on May 9, 2002.

(51) Int. Cl.

| C12Q 1/00 | (2006.01) |
|---|---|
| C12Q 1/02 | (2006.01) |
| C12Q 1/04 | (2006.01) |
| C12M 1/36 | (2006.01) |
| C12M 1/38 | (2006.01) |
| C12M 1/00 | (2006.01) |
| C12M 3/00 | (2006.01) |
| C12M 1/34 | (2006.01) |
| C12N 11/00 | (2006.01) |
| C12N 11/16 | (2006.01) |
| G01N 33/53 | (2006.01) |
| G01N 33/569 | (2006.01) |
| G01N 33/554 | (2006.01) |
| G01N 33/543 | (2006.01) |

(52) U.S. Cl.
USPC ............ 435/4; 435/7.2; 435/7.22; 435/7.32; 435/29; 435/34; 435/174; 435/286.5; 435/287.2; 436/518

(58) Field of Classification Search
USPC .......... 422/50, 55, 58, 68.1, 101, 104; 435/4, 435/7.1, 286.4, 287.1, 287.2, 288.3–288.5, 435/288.7; 436/501, 164, 165, 175, 177, 436/178
See application file for complete search history.

(56) References Cited

U.S. PATENT DOCUMENTS

| 5,624,815 A | * | 4/1997 | Grant et al. ................ 435/30 |
| 5,650,323 A | * | 7/1997 | Root ....................... 435/284.1 |
| 5,660,990 A | * | 8/1997 | Rao et al. .................... 435/6 |
| 5,716,798 A | * | 2/1998 | Monthony et al. ............ 435/34 |
| 5,770,440 A | | 6/1998 | Berndt |
| 6,043,027 A | * | 3/2000 | Selick et al. .................. 435/4 |
| 6,372,183 B1 | * | 4/2002 | Akong et al. ................ 422/63 |
| 6,377,721 B1 | * | 4/2002 | Walt et al. .................... 385/12 |
| 6,696,286 B1 | * | 2/2004 | Halverson et al. ......... 435/287.9 |
| 6,716,629 B2 | * | 4/2004 | Hess et al. ................... 435/420 |
| 6,729,352 B2 | | 5/2004 | O'Connor et al. |
| 6,743,581 B1 | | 6/2004 | Vo-Dinh |
| 6,767,706 B2 | | 7/2004 | Quake et al. |
| 6,818,435 B2 | | 11/2004 | Carvalho et al. |
| 6,852,222 B2 | * | 2/2005 | Clark et al. .............. 210/321.75 |
| 7,125,674 B2 | * | 10/2006 | Beattie ........................ 435/6 |
| 8,067,154 B2 | * | 11/2011 | Gazenko ...................... 435/4 |
| 8,361,783 B2 | * | 1/2013 | Gazenko .................. 435/287.2 |
| 2002/0153046 A1 | * | 10/2002 | Dantsker et al. ............. 137/833 |
| 2002/0172621 A1 | * | 11/2002 | Barbera-Guillem .......... 422/100 |
| 2002/0189374 A1 | * | 12/2002 | DeSilets et al. ............ 73/864.51 |
| 2003/0096268 A1 | * | 5/2003 | Weiner et al. ................. 435/6 |
| 2005/0009113 A1 | * | 1/2005 | Goldbard et al. ............ 435/7.2 |
| 2005/0221403 A1 | * | 10/2005 | Gazenko ................... 435/7.32 |
| 2006/0088895 A1 | | 4/2006 | Wanders et al. |

OTHER PUBLICATIONS

Martin, Paul, Office Action for U.S. Appl. No. 11/393,012, entitled "Method and device for rapid detection of microorganisms by changing the shape of micro-colonies," mailed Feb. 19, 2008 (1).

Ford, Vanessa L, Office Action for U.S. Appl. No. 10/141,677 entitled "Micromethod and Device for Rapid Detection, Enumeration and Identification of Entities," mailed Aug. 20, 2008. (9).

Ford, Vanessa L, Office Action for U.S. Appl. No. 10/141,677 entitled "Micromethod and Device for Rapid Detection, Enumeration and Identification of Entities," mailed Nov. 29, 2007 (8).

(Continued)

*Primary Examiner* — Nita M Minnifield
(74) *Attorney, Agent, or Firm* — Acker Wood IP Law, LLC; Gwen R. Acker Wood (57) ABSTRACT

This invention describes a device consisting of a micro channel plate, filter, and porous holder for filter, which is substituted by a pure agar block during method performance, and supportive structural elements. The device is intended for rapid detection and/or identification of microorganisms. Microorganisms are trapped by filtration in long (diameter/length=1/10-1/100), cylindrical, parallel, micro-channels that are open from both sides and attached to a filter from one side. A micro channel plate houses a multiplicity of micro channels (possible diameter of each channel=1-30 μm, length 100-1000 μm, and number on centimeter$^2$=100,000-1,000,000). The micro channel plate with cells trapped on the surface of the filter is attached to an agar block impregnated by artificial substrate(s) so that the molecules of the artificial substrates will fill all micro channels. Trapped cells produce colored or fluorescent molecules from artificial substrates. These molecules are collected in the very small volume of a micro channel. The extremely small volume of a micro channel (1/25 million part of milliliter) allows it to collect a detectable concentration of color or fluorescent substances in a very short time (several minutes). Even one cell from a filtrated sample can be detected by the enzyme—artificial substrate method and/or identified by enzyme immunoassay.

21 Claims, 10 Drawing Sheets

(56) References Cited

OTHER PUBLICATIONS

Ford, Vanessa L, Office Action for U.S. Appl. No. 10/141,677 entitled "Micromethod and Device for Rapid Detection, Enumeration and Identification of Entities," mailed Jun. 14, 2007 (7).

Ford, Vanessa L, Office Action for U.S. Appl. No. 10/141,677 entitled "Micromethod and Device for Rapid Detection, Enumeration and Identification of Entities," mailed Feb. 8, 2007 (6).

Ford, Vanessa L, Office Action for U.S. Appl. No. 10/141,677 entitled "Micromethod and Device for Rapid Detection, Enumeration and Identification of Entities," mailed Jun. 1, 2006 (4a).

Ford, Vanessa L, Office Action for U.S. Appl. No. 10/141,677 entitled "Micromethod and Device for Rapid Detection, Enumeration and Identification of Entities," mailed Jul. 27, 2005 (4).

Ford, Vanessa L, Office Action for U.S. Appl. No. 10/141,677 entitled "Micromethod and Device for Rapid Detection, Enumeration and Identification of Entities," mailed Sep. 8, 2004 (3).

Ford, Vanessa L, Office Action for U.S. Appl. No. 10/141,677 entitled "Micromethod and Device for Rapid Detection, Enumeration and Identification of Entities," mailed Dec. 12, 2003 (2).

Ford, Vanessa L, Office Action for U.S. Appl. No. 10/141,677 entitled "Micromethod and Device for Rapid Detection, Enumeration and Identification of Entities," mailed May 30, 2003 (1).

Harle, Jennifer, Office Action for U.S. Appl. No. 10/628,110, entitled "Method for rapid detection of microorganisms by changing the shape of micro colonies," mailed Oct. 27, 2005 (2).

Harle, Jennifer, Office Action for U.S. Appl. No. 10/628,110, entitled "Method for rapid detection of microorganisms by changing the shape of micro colonies," mailed Nov. 9, 2004 (1).

Baharlou, Simin, International Preliminary Report on Patentability (IPRP), International Application No. PCT/US2006/015321, entitled "Device for Rapid Detection and Identification of Single Microorganisms Without Preliminary Growth," mailed Nov. 1, 2007.

Martin et al. Generation of larger numbers of separated micorbial populations by cu8ltivation in segmented-flow microdevices; Lab-on-a-Chip, vol. 3 (2003) pp. 202-207.

Yang et al., "Cell Docking and On-Chip Monitoring of Cellular Reactions with a Controlled Concentration Gradient on a Microfluidic Device" Analytical Chemistry, vol. 74, No. 16 (2002) pp. 3991-4001.

Thiebaud et al., "PDMS device for patterned application of microfluids to Neuronal cells arranged by microcontact printing"; Biosensors and Bioelectronics, vol. 17 (2002) pp. 87-93.

Walker et al., "Insect Cell Culture in Microfluidic Channels" Biomedical Microdevices, vol. 4, No. 3 (2002) pp. 161-166.

\* cited by examiner

Funnel for liquid samples attached to device containing MCGP

Syringe for liquid and semi liquid samples and antibody-enzyme conjugates

Device contains MCGP opens for bioaerosols sampling

To Air pump.

DEVICE FOR RAPID DETECTION AND IDENTIFICATION OF SINGLE MICROORGANISMS WITHOUT PRELIMINARY GROWTH

The present application is a continuation application of U.S. patent application Ser. No. 10/141,677, filed May 9, 2002, now U.S. Pat. No. 7,781,159, which is incorporated by reference herein.

BACKGROUND OF THE INVENTION

1. Field of the Invention

Modern microbiological diagnostics and analysis serves for detection, enumeration, and identification of microorganisms present in different samples. In the areas of medical diagnostics and veterinary medicine, these organisms are pathogenic or dangerous microbes in human or animal blood, internal organs, skin, tissues, respiratory organs, and so on. In the area of industrial microbiology, microbes commonly pollute technological processes, materials, equipment, and finished products. In environmental analysis, there is often microbial contamination of water, indoor and outdoor air, and various surfaces. In epidemiology and biodefense—highly contagious pathogenic microorganisms from human body or environment.

Time, quality, and sensitivity of microbiological analyses are crucial for two reasons. First, tens of thousands of domestic microbiological laboratories spend several billions of dollars annually for products and processes quality control and prevention of contamination and spoilage in industry. These laboratories also spend money to provide diagnostic tests for humans, animals, plants, food, personal care products, soil, and environment. A quick, reliable, streamlined diagnostic test can save companies millions of dollars in the long run. Second, several thousands of people die even in such highly developed countries as the United States because of a delay in medical treatment caused by long-term diagnostics. Decreasing the time it takes to run these microbiological diagnostics tests will result in an increase of analysis reliability and sensitivity. Ultimately, this can save thousands of human lives worldwide.

This invention is a device for rapid detection and identification of microorganisms without preliminary growth.

2. Description of the Related Art

Modern methods of detection, enumeration, and identification of microorganisms can be divide into two main parts: 1) the methods and devices that need preliminary growth (enriching) to create a detectable amount of cells; 2) methods that don't need preliminary growth because they are capable of analyzing as little as a single cell.

The first group includes growth in solid or liquid regular or selective nutrient medias. It also includes several immunological methods. Examples are latex and hemagglutination, antibodies on magnetic particles, enzyme immunoassays like ELISA and Western Blot, and "deepstick" methods. The first group also includes chromatography of fatty acids, infrared Raman and FTIR spectroscopy, mass-spectrometry, and ATP-, bio-, and chemiluminescence. These methods require hundreds to millions of pure cells for detection of a certain microorganism, and, therefore, long (many hours or days) preliminary growth.

The second group of methods and devices does not need preliminary growth because they are capable of detecting and/or identifying even a single cell. These methods and devices consist of a group of nucleic acid methods like PCR and its various modifications, Epi-fluorescent methods (fluorogenic substrate methods, immunofluorescence), and a group of Flow Cytometry methods.

In addition to other drawbacks, methods of detection and/or identification of cells without preliminary growth usually need very expensive and sophisticated equipment and the work of high-level professionals. For example, devices used for PCR include the expensive thermocycler and sophisticated fluorometer. PCR is also used only for identification purposes. Enumeration of initial contamination is not reliable with PCR usage. PCR is very sensitive to organisms which can contaminate the test itself.

Epi-fluorescence usually needs only a fluorescent microscope to detect a single cell marked by a fluorescent dye or fluorescent antibody (Ab+fluorochrom). However, the amount of fluorescent substance present is restricted by volume of the cell body or cell surface. The small size of the object (single microorganism) makes the detection of one cell very difficult, especially with large background fluorescence usually present in a majority of the samples. Substances that flow out of a cell or enzyme immunoassay of a single cell are impossible with Epi-fluorescent methods because these indicator substances disperse in the surrounding space immediately but are not concentrated in a small volume like proposed by the current invention.

Flow Cytometry is based on a very complicated opto-electronics system. A flow cytometer consists of a sophisticated optical block, a block of electronics, a complicated hydrodynamic system, and a high-speed computer. Prices for different types of flow cytometers range from $50,000 to $140,000. Flow cytometers can analyze one single cell during its flow through channels with diameters of 10 microns each. This size of the channel is so narrow that it needs 17 hours to pass 100 ml of liquid through it, even if speed of flow is 20 meters per second. Therefore, flow cytometers are currently used in hematology because of large (5-6 million/ml) and more or less stable concentrations of blood cells. Also, flow cytometers very effective as sorters of cells mixtures in cytology. Usage of flow cytometry in microbiology is not easy. In microbiology these instruments are not often used because microorganisms can create clusters with other particles and can be confused with natural particles or dead cells. If the concentration of cells in a sample is very small, the time of analysis goes up dramatically. Therefore, preliminary concentration or even enriching is needed for Flow Cytometry microbiological applications. Microbes are also much more diverse by size and shape than blood cells and, thus, mistakes occur very often.

It is known, and currently used in practice, that dividing a sample into small volumes helps to detect cell concentration faster. This effect depends on reaching a detectable concentration in a small volume faster than in a large volume. U.S. Pat. No. 5,716,798 describes the method for rapid detection of microorganisms in a container divided on a plurality of discrete zones, each of which can be separately monitored for microbial presence by reaching detectable cell concentrations after preliminary growth in some zones. This method gives time-saving of 10% to 40% in comparison with other methods. U.S. Pat. No. 5,770,440 is based on the same effect. The present invention differs from these patents because of the analysis of a single cell. No time-consuming preliminary growth or nutrient media are necessary.

U.S. Pat. No. 4,959,301 is based on dividing a sample with viable biological entities into micro-droplets and detecting entities by growth or by biochemical reactions of a single entity within a droplet. This method can indicate a single cell in less than 30 minutes in some variants. Nevertheless, it is technologically complicated. Micro-droplets are produced with different volumes and require statistical analysis for calculating results. This method could be reproduced only in a laboratory by highly professional personnel with use of sophisticated and expensive equipment.

The proposed device has significant advantages in comparison with known methods:

It is capable of detecting and/or identifying by colored or fluorescent enzyme or enzyme-immunoassay as little as one single cell trapped in a micro-channel (one cell in one micro-channel corresponds to a concentration of 25 million cells per ml). Thus, no preliminary growth is needed, and a detectable concentration is reached in several minutes.

The price of the device and analysis is tens times less than Flow Cytometry or PCR (only a regular fluorescent or light microscope is needed for this diagnostic device). Also, the amount of reagent needed is substantially less than with the use of regular 96-well plates. As a result, the analysis is simple and cost-effective.

The device is simple to use and involves performing only regular filtration with just a few manipulations. Even non-specialists can easily adopt this device and procedure that is very important for their broad use.

Many different methods can be applied with the proposed device: detection of live cells by fluorogenic or chromogenic substrate(s), differentiation by special enzymes and artificial substrate(s) for them, identification by enzyme immunoassay of one single cell, analyzing of different liquid or air samples.

These advantages promise excellent opportunities for implementation of this device and its versions in medical diagnostics, industry, environmental science, and biodefense.

BRIEF SUMMARY OF THE INVENTION

This invention constitutes a device consisting of a micro channel plate, supportive structural elements, filter, and a filter holder, which is substituted by a pure agar block or nutrient media block during method performance. The device is intended for rapid detection and/or identification of microorganisms by providing biochemical enzymological or enzyme immunoassay reactions in a very small volume of the micro channel. Even one single cell trapped in a micro channel could be detected or/and identified in a time range of several minutes to tens of minutes.

Microorganisms are trapped by filtration on the surface of filtrating material in long (diameter/length=1/10-1/100), cylindrical, parallel, micro channels that are open from both sides, and attached to a filtration material from one side. A micro channel plate houses a multiplicity of micro channels (possible diameter of each channel=1-30 μm, length 100-1000 μm, and number on one $cm^2$=100,000-1,000,000). After filtration is completed, the device is untwisted and the filter holder removed and substituted by a pure agarose block. The pure agarose block (agar) is filled by a biochemical indicator (artificial substrate(s) for enzyme(s)—chromogenic or fluorogenic, depends on method) reagent in advance. Molecules of the artificial substrate and solvent fill all micro channels and natural enzyme(s) of a live cell or enzyme attached to the cell surface through an antigen—antibody reaction (enzyme immunoassay for single cell), which starts a transformation of colorless artificial substrate molecules into colored or fluorescent molecules. These molecules collect in a very small volume of micro-channel containing a cell. The extremely small volume of a micro-channel (1/25 million part of milliliter) allows it to collect a detectable concentration of colored or fluorescent substance in a very short time. The volume of one micro-channel is so small (only 40,000 cubic micrometers in the case of micro channel's dimensions: diameter 10 micrometers and longevity 500 micrometers) that one single cell trapped in a micro-channel corresponds to a concentration of 25 million cells per milliliter of sample. Micro-channels containing cells and concentrated colored (violet, blue, dark blue, black or other—depends on used chromogenic substrate) molecules look like colored round spots on a bright background under a regular light microscope. Micro channels containing cells and concentrated fluorescent molecules look like bright (blue, green, red—depends on used fluorogenic substrates) round spots on a dark background under a fluorescent microscope. The number of colored or fluorescent spots (dots) corresponds to the number of live cells in the initial filtrated sample or the number of special dangerous or pathogenic cells identified by enzyme immunoassay. A simple observation and count of colored or fluorescent dots on the surface of the micro channel plate allows for rapid and reliable detection and/or identification and enumeration of cells in concentration of as little as one single cell per sample.

BRIEF DESCRIPTION OF THE SEVERAL VIEWS OF THE DRAWINGS

The process of depositing of magnetic particle on the bottom of micro-channel and it separating from non-magnetic particles shows below.

DETAILED DESCRIPTION OF THE INVENTION

This invention constitutes a device for rapid detection and/or identification of cells in concentrations up to a single cell present in an investigated sample without preliminary growth. This goal is reached by filtration of the investigated sample through a device consisting of a micro-channel plate, filter, and a holder for the filter, which is substituted during the procedure by an agarose block filled with reagents. The device is surrounding by a supportive frame. During filtration microorganisms pass through micro-channels and are trapped on the surface of the filter. After filtration is complete, micro-channels are filled by reagents from the agarose block, and a reaction between cellular enzymes and artificial substrate(s) begins. The product of these reactions (colored or fluorescent molecules) fills the volume of the micro-channel rapidly because of its extremely small inner volume. The product will quickly reach a detectable concentration seen under light or fluorescent microscope. Micro-channels containing cells look like colored or fluorescent dots easily distinct from empty micro-channels.

Figure 1:
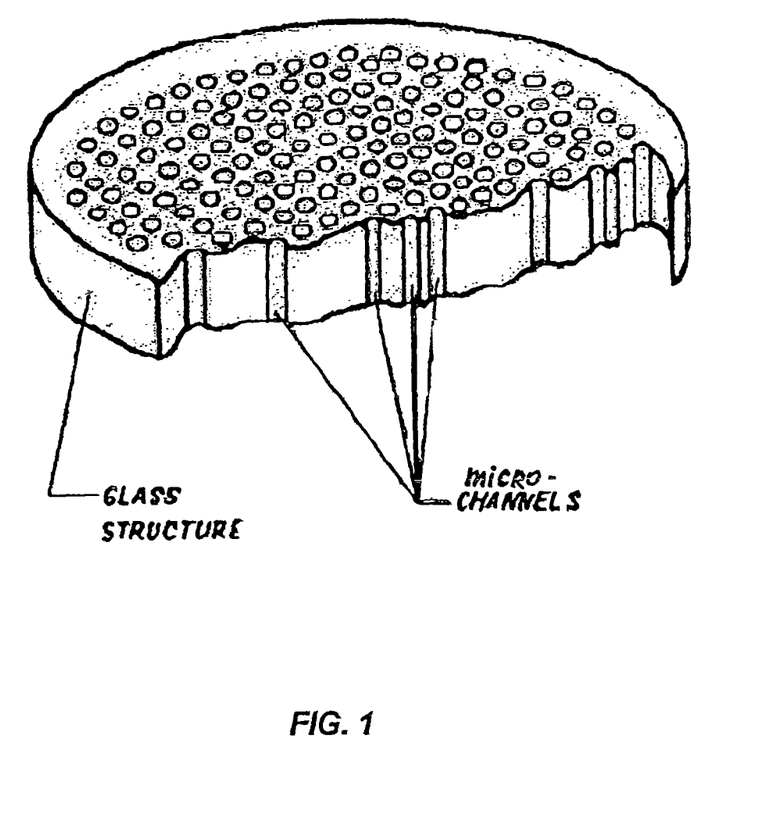
FIG. 1. Shows general structure and shape of the micro channel glass plate. Micro channels shown relatively big in comparison with plate. The real size of channels on this plate is: diameter of the channel 10 micrometers, longevity 500 micrometers, distance between channels 2 micrometers and number of channels is around 700,000 per $cm^2$.

The crucial part of the described device is a micro-channel plate (FIG. 1). The micro-channel plate is made of a glass disc that can contain thousands or millions of tiny, precisely manufactured channels (pores). Deviation of the micro-channels' size and volume usually doesn't exceed 1%. The channels are typically 1-20 microns in diameter and have a length 10-100 times longer than their diameter. The volume of one channel could be from 1000 to 300,000 $\mu m^3$. A micro-channel plate may contain 100,000-1,000,000 channels per $cm^2$. The distance between channels is approximately 1-2 $\mu m$. The diameter of a plate could be varied. Usually it is 25-47 mm. Thickness of plates ranges from 0.2 to 5 mm (usually 0.5 mm).

One single cell trapped in the channel (length—500 $\mu k$, diameter of channel—10 $\mu k$, volume—40,000 $\mu k^3$) corresponds to a concentration of 25 million cells per ml. Thus, a detectable concentration of analytical (colored or fluorescent) substances from one cell will be reached in the same time that 25 million analogous cells are capable of producing. This time is several minutes or several tens of minutes, depending on the cells present and the method used. Another example of the effectiveness of micro volumes: concentration of a fluorescent substance which is visible by the naked eye (4-Methilumbelliferone from 4-Methilumbelliferyl acetate) is reached by one cell (Bacillus megatherium) in micro channel (volume=40,000 $\mu k^3$) in two minutes. The same cell in one milliliter (volume=$10^{12}$ $\mu m^3$) will produce the same concentration after 95 years.

The micro-channel plate is made from a special glass. It is resistant to the different solvents or glass cleaning solutions. The micro-channel plate is also physically durable. The micro-channel can be made from black nonfluorescent glass or from none colored glass.

Micro-channels exhibit extremely strong capillary forces because of the very small diameter of the channels (capillaries). In fact, its capillary forces are powerful enough to raise a column of water up to a hundred meters. Even highly viscous liquids like Glycerol can easily fill the channels. Therefore, micro-channels will fill with liquids from an agarose block attached to the underside of the plate in a matter of seconds.

Currently produced by industry, micro-channel plates used for image intensifiers are not enough suitable for microbiological purposes of the invented device because their channels are manufactured under a special angle to the surface of the plate. This does not give the plate reader a chance to observe the entire inner volume of the micro-channel under a microscope The optimal angle for viewing the channels is exactly 90°. Also, the production process of plates needs to be changed in order to produce colorless plates to use for color reactions.

The micro-channel plate shown on FIG. 1 has relatively big and short (small ratio of length/width) channels only for demonstration purposes. The real dimensions of the micro-channel plate used in this invented device are: diameter of the channel=10 $\mu m$, length of channel=500 $\mu m$, number of micro-channels on one $cm^2$ around 700,000, diameter of the plate 25 mm. It is possible to produce micro-channel plates with other parameters. The modern price of one micro-channel plate falls within a range of $50-$300. Each micro-channel plate can be used at least one hundred times for analytical purposes in the invented device.

Figure 2:
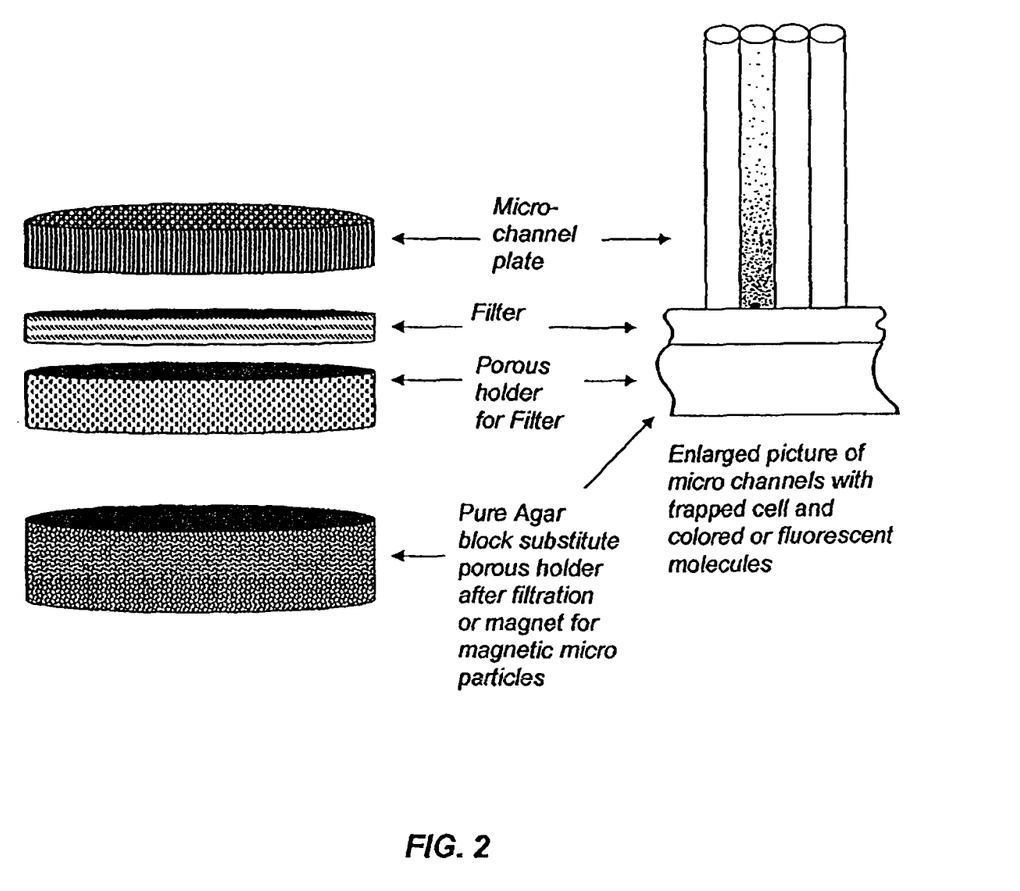
FIG. 2. Explains main parts and general structure of the device for sampling, detection, and/or identification of microorganisms. Left side of picture explains position of the main components: micro channel plate, filter, filter holder, and agar block. Right side shows a part of the structure at large magnification. Production of fluorescent or colored molecules from one cell trapped in micro channel is shown in the channels.
Figure 3:
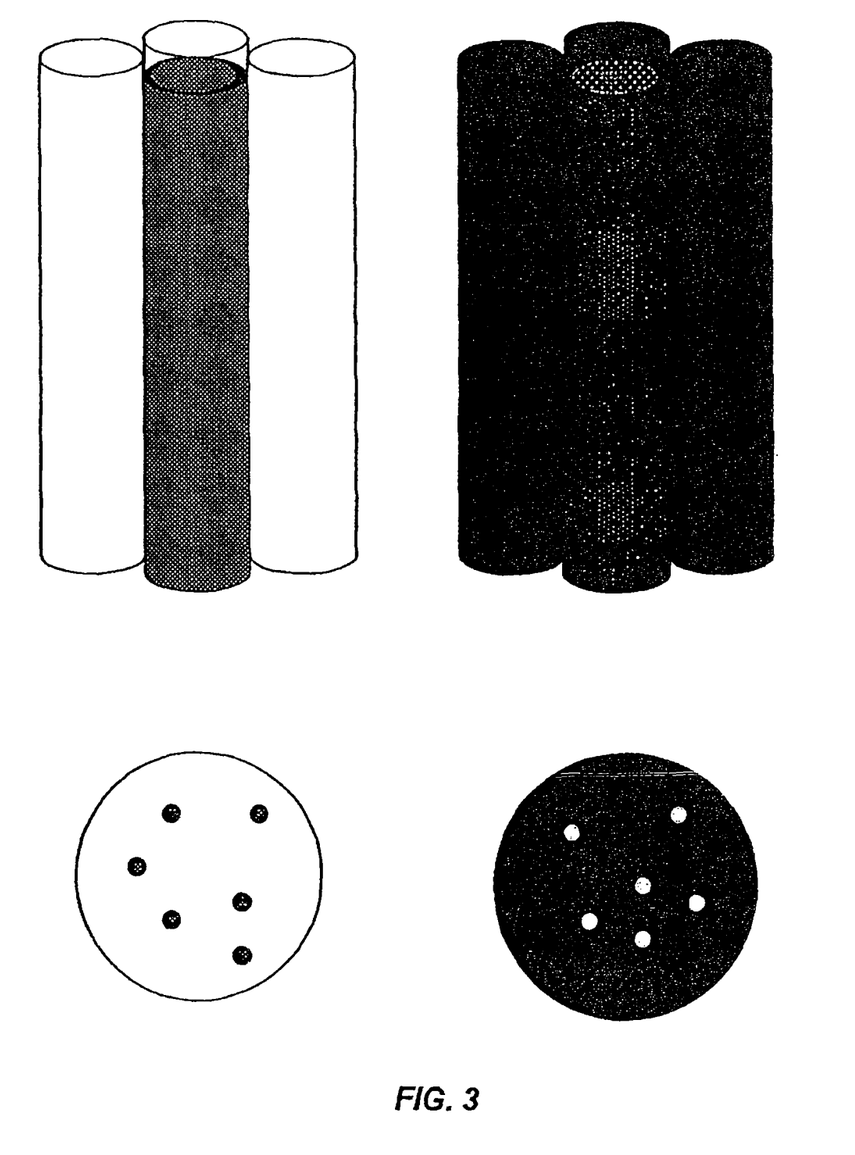
FIG. 3. Shows differences between micro channels filled by colored molecules (left) and fluorescent molecules (right). Pictures below explains how both versions looks under light or fluorescent microscopes.

The main parts of the device ready for filtration are shown in FIG. 2. The device consists of a micro-channel plate, filter, and a holder for the filter or agar block filled by artificial substrates. This structure is surroundings by a frame as shown in FIG. 3 (assembled) and FIG. 4 (taken apart): 1—frame for plate, filter and filter holder done from plastic; 2—rubber ring to prevent sudden damage of micro-channel plate and unlikable slots between frame and plate; 3—micro-channel plate; 4—filter for trapping cells; 5—holder for filter able to pass liquids (liquid samples) or air (bioaerosols) done from plastic or glass particles; 6—rubber ring for gently pressing holder for filter during filtration; 7—plastic funnel for adjusting of the device to filtrating manifold (see FIG. 7 also). The upper part (1-5) stays together with the plastic funnel (7) by screw-in (frame (1) to funnel (7)) or by friction.

Figure 9:
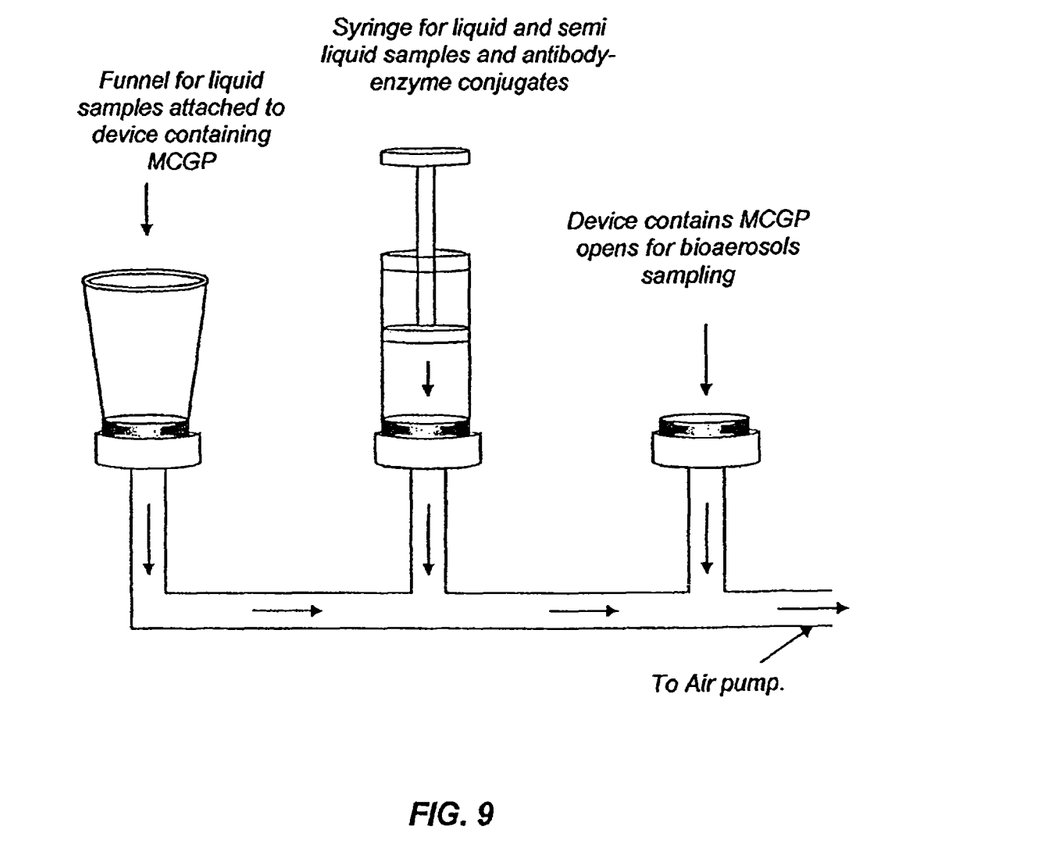
FIG. 9. Demonstrate position of device during filtration process: device with funnel for liquid samples (left), device with syringe for adding antibody-enzyme conjugate (center), device during air (bioaerosols) filtration (right).

The procedure of filtrating is shown on the FIG. 9. The assembled device is attached to the manifold for filtrating. Negative pressure from the pump passes liquid or air samples through the micro-channel plate. Cells present in the sample are trapped in some of the micro-channels on the surface of the filter.

Figure 7:
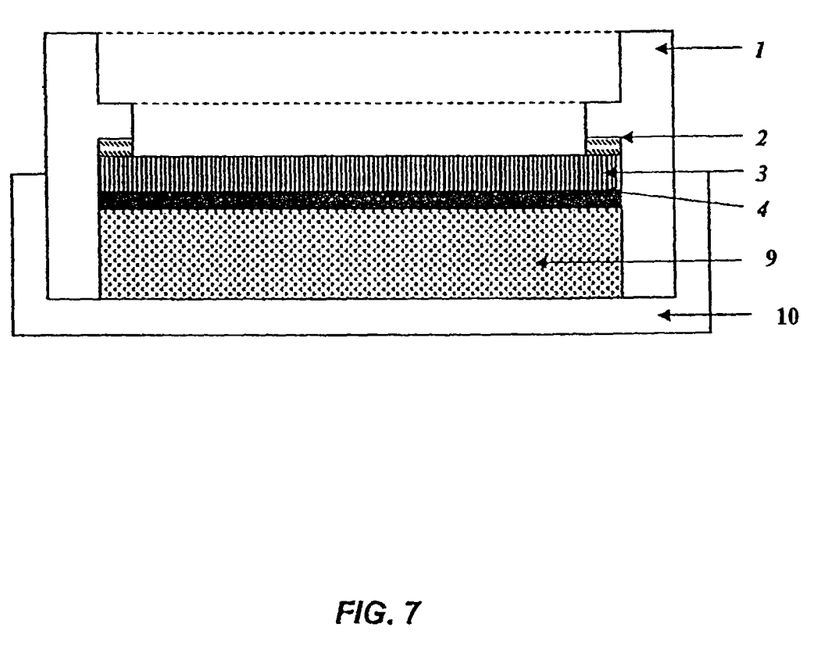
FIG. 7. After filtration is done the upper part of the device is removed from the filtrating lower funnel. Filter holder is removed and substituted by pure agar block (5). Device shown on this picture is a result of these transformations.
Figure 8:
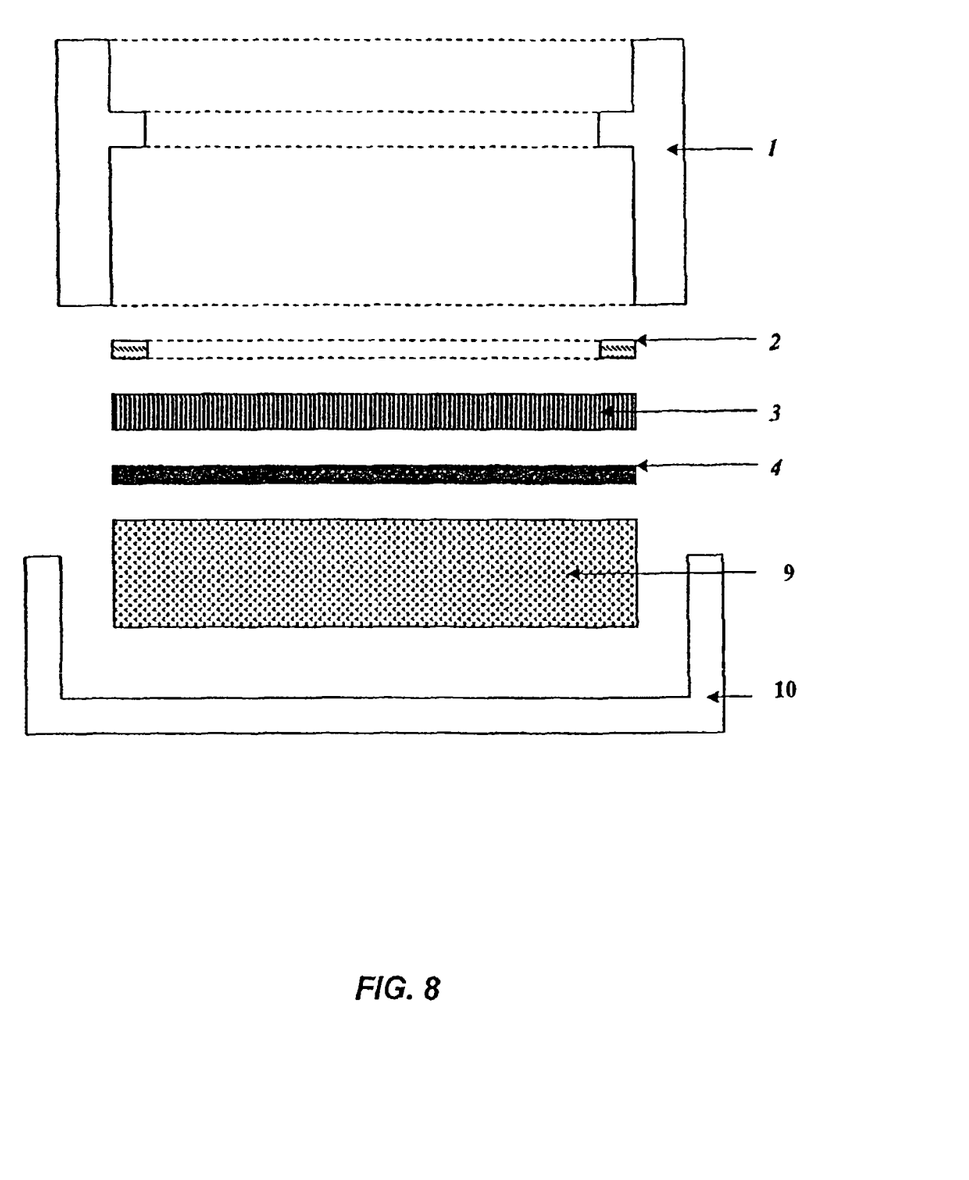
FIG. 8. This picture shows unassembled components of the device shown on FIG. 7.

When the filtrating process is complete and no more liquid is present inside the micro-channels, the device is removed from the manifold and untwisted. The plastic holder for the filter is removed, and the block with artificial substrate(s) is installed in its place (FIGS. 7 and 8). Immediately, all micro-channels fill with artificial substrate solution and a reaction takes place between enzymes of live cells or enzymes attached to the cellular surface through antibody (enzyme immunoassay). This process takes place in a significantly different (modified) device shown in FIG. 7-8. FIGS. 7 and 8 demonstrate an assembled device containing: 1—frame for plate, filter, and filter holder done from plastic; 2—rubber ring to prevent sudden damage of micro-channel plate and unlikable slots between frame and plate; 3—micro-channel plate, 4—filter for trapping cells, 9—agarose block filled by artificial substrates which in solution fill micro-chanenls; 10—plate for agar block and attachment to frame 1. Plate 10 can be screwed up to frame 1 or just kept in place by friction. After needed changes are done, this modified device is placed in an incubator in order to create a detectable amount of colored or fluorescent molecules in micro-channels containing targeted microorganisms.

Agar Block and Artificial Substrates

Figure 5:
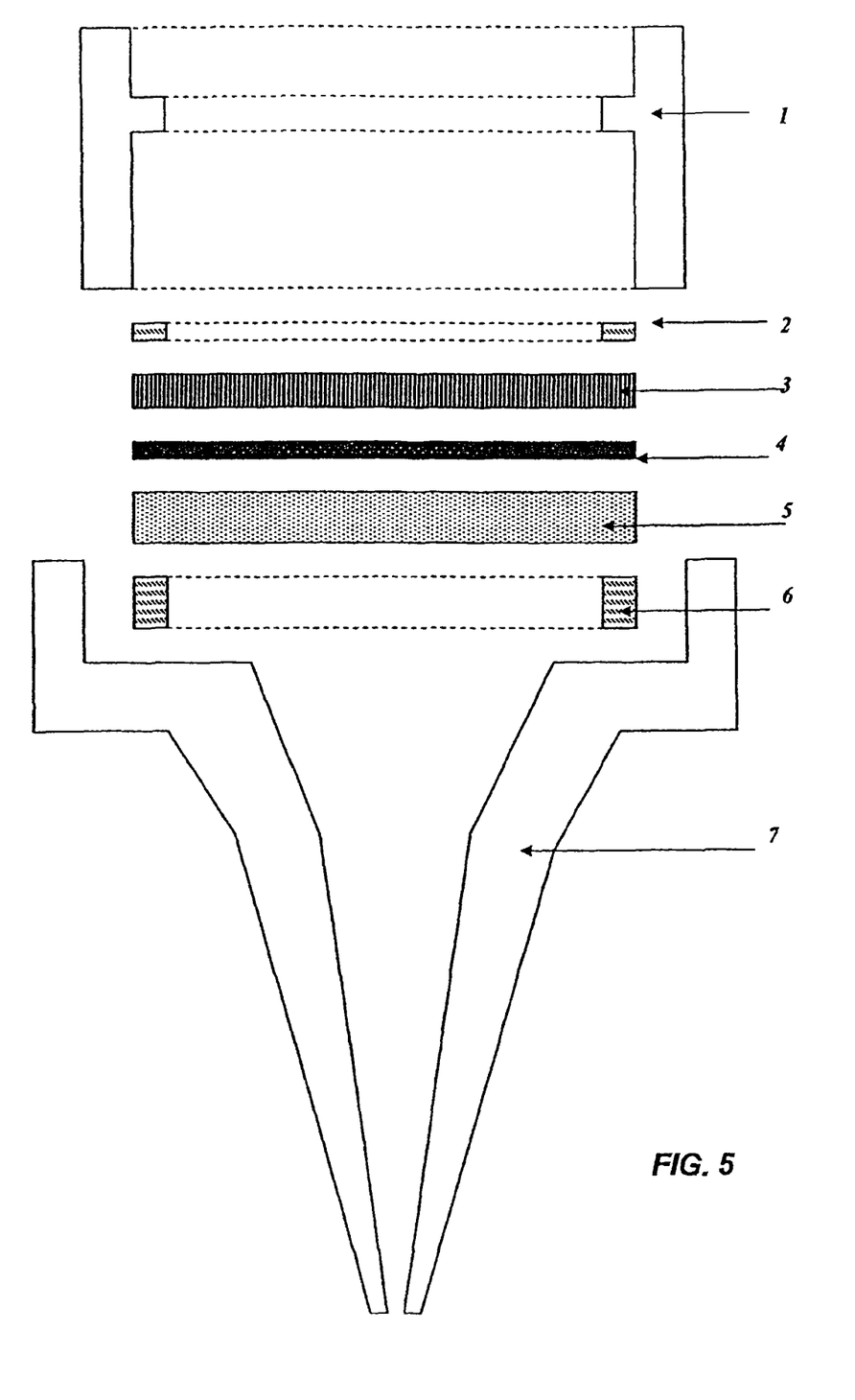
FIG. 5. Shows components of the same device as on FIG. 4 unassembled

The artificial substrates for different enzymes or enzymatic groups for the production of detectable concentrations of absorbent or fluorescent molecules are well-known. Artificial substrates are used for detection of enzymatic activities, live cell detection, and identification in enzyme immunoassay and ELISA. The main feature of artificial substrates is their ability to create colored or fluorescent molecules after transformation by enzymes. Many different artificial substrates are based on chromogenic molecules such as 2-Nitrophenol, 4-Nitrophenol, 5-Bromo-4-chloro-3-indoxol, 3-Inoxol, 5-Bromo-chloro3-indoxol, 6-Chloro-3-indoxol, 5-Iodo-3-indoxol, N-Methylindoxol, 3,3'5,5'-Tetramethylibenzidine dihydrochloride, Tetrazolium salts, and others. Other artificial substrates are based on fluorescent molecules such as 4-Methylumbelliferone, 7-Amido-4-methylcoumarin, Fluorescein, Eosine and others. They cover a large spectrum of different enzymes such as Glycosidases, Esterases, Phosphatases, Peptidases, Sulfatases, Dehydrogenases, and special enzymes like Horseradish-Peroxidase, β-D-galactosidase, or a specific aminopeptidase. Some colored or fluorescent molecules produced from artificial substrates are collected inside the cell, while some of them go outside and are collected in the extracellular environment. Molecules collected inside the cell (Tetrazolium salts, 5-Iodo-3-indoxol, Fluorescein, and other) are important for Flow Cytometry and Epi-fluorescence because they color the cell body and make it more visible or/and detectable. This is a very small amount of molecules because it is restricted by the volume of cell. The collecting of these molecules inside a cell can cause cell death. Other group of molecules/substances has the ability to flow out of the cell during enzyme—substrate reactions (4-Methylumbelliferone, 7-Amido-4-methylcoumarin, 4-Nitrophenol and other). They do not cause cell death and therefore can collect for a long time and reach large concentrations. This group of artificial substrates is used for creating methods of detection and identification with the invented device because molecules collected in the micro-channel with the cell color them or make them fluorescent as shown in FIG. 5. The left side of FIG. 5 demonstrates the difference between a micro-channel filled by colored molecules as a result of a color reaction and micro-channels without cells. The circle below demonstrates colored micro-channel under a microscope. The right side of FIG. 5 demonstrates the differences between micro-channels filled by fluorescent molecules and micro-channels without cells. The circle below demonstrates micro-channels filled by fluorescent molecules under a microscope.

Delivery of artificial substrates in micro-channels can be done with the help of an agarose cylindrical block filled by the needed artificial substrate (FIG. 2, FIG. 7 and FIG. 8).

The advantage of the block filled with agarose gel (agar) is that dissolved substances (substrates) are not anti to molecules-polymers of agar and therefore can easily go out and fill all micro-channels because of their strong capillary forces; the agar block can be squeezed in each direction and therefore easily fit to the surface of the filter without holes or slots. No one known artificial substrate does not react with agarose molecules. The agar block can be cut out from an agar layer or prepared by solidifying in special form. Agar is transparent to light and therefore can be used under a light microscope without removing.

Other gels like gelatin, silica gels or polyacrylamide gel or even other carriers of soluble substrates like filter paper can be used in some cases as well.

Version of Device for Colored (Light Absorbent) Reactions

The device used for color (light absorbent) reactions and molecules must have colorless a microchannel plate and colorless or white filter. Colorless micro-channel plate and filter are transparent for light and colored micro-channels are observed better with a light microscope in the light mode.

Version for Fluorescent Reactions

The black micro-channel plate and black filter must be used in this version in order to eliminate possible background fluorescence.

Version for Particles (Coated by Antibodies Non-Magnetic, Magnetic and Paramagnetic Microparticles)

The invented device can be used for depositing in micro-channels not only cells but also particles coated by antibodies. These particles need to be significantly less than the diameter of the micro-channels. Particles coated by a specific monoclonal antibody (polypropylene, polycarbonate, magnetic and other) are broadly available on the diagnostic market. Coated particles are used for concentration of antigens (bacteria, viruses, proteins, and so on) on their surface by Ab-Ag interaction. Thus, particles coated by an antibody for an investigated virus will adsorb viruses on their surface and after filtration through device, they will deposit in the micro-channels. Coated particles give opportunities to deposit in micro-channels small objects like viruses, proteins, and other biomolecules that could not be captured by regular filtration because of small size. After coated particles with separately adjusted viruses or biomolecules are trapped in the micro-channels, they can be identified by the enzyme immunoassay described above.

Figure 10:
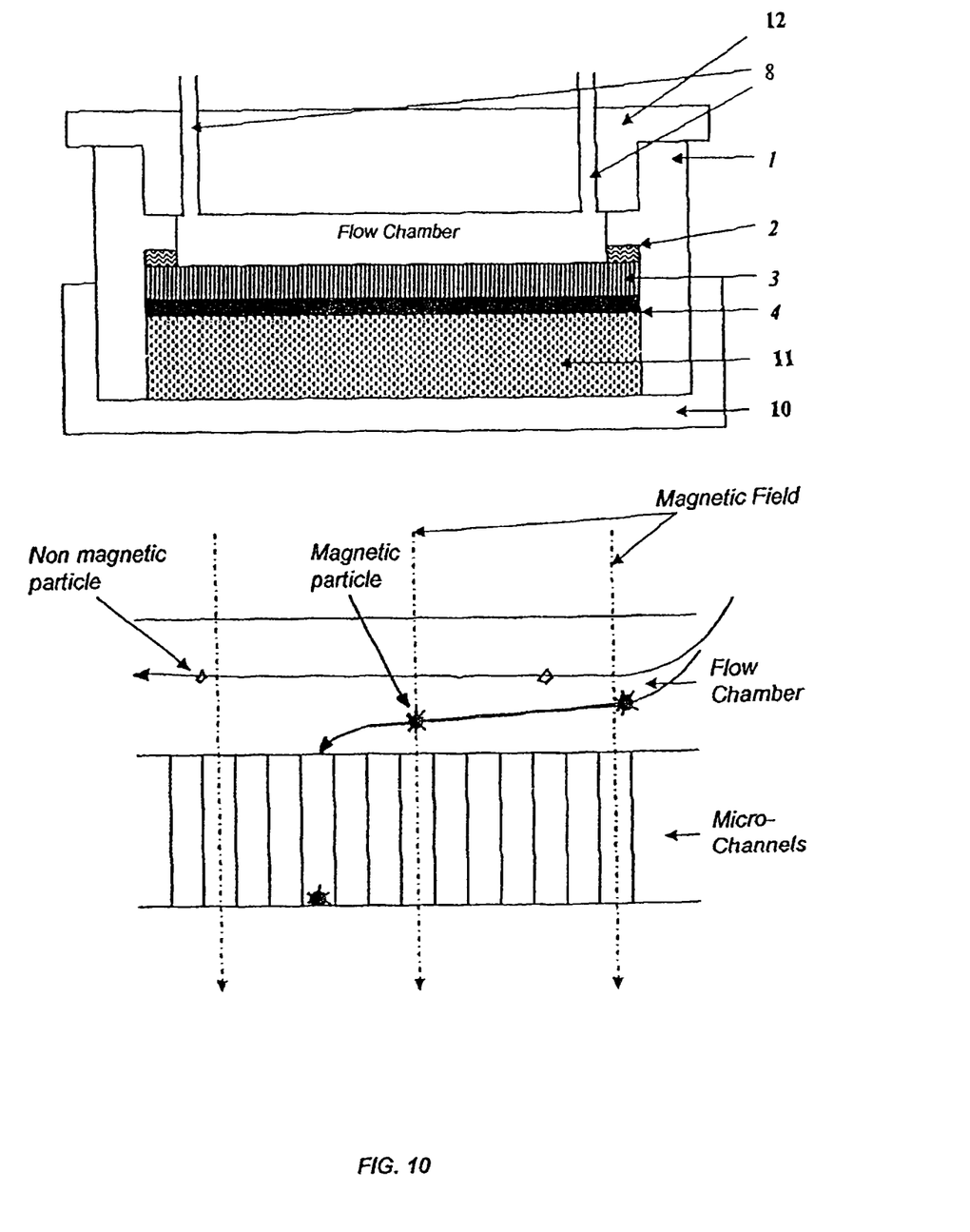
FIG. 10. Shows the general structure of the Device transformed for depositing of magnetic particles with bio-particles (cells, viruses, biomolecules) adjusted to the surface of magnetic particle through Ab-Ag interaction in micro-channels.

Magnetic particles can be trapped in micro-channels by a magnetic field. In this case, the agar block shown in FIG. 7 must be substituted by a magnet. The magnet must be strong enough to pull magnetic particles from liquid to the bottom of the micro-channel as shown in FIG. 10. The ability to pull magnetic particles with antigens on the surface of filtration material from a liquid stream depends on the energy of the magnetic field, concentration of Iron, Cobalt and rare earth atoms, and/or size of particle and speed of stream. All these parameters can be easily adjusted for the specific needs of a sample in order to pull all magnetic particles from the stream and let non-magnetic particles (organic and mineral particles, live and dead cells without needed antigen determinants and solvent molecules) flow out of the device flow chamber.

This version of the device has an additional element: a lid with channels for input and output liquid loaded by magnetic particles with cells, viruses, or molecules attracted to their surface. FIG. 10 shows the structure of this modified device: 1—frame for plate, 2—rubber ring to prevent sudden damage of micro-channel plate and unlikable slots between frame and plate filter, and filter holder done from plastic; 3—micro-channel plate; 4—filter for trapping cells; 11—Iron or rare earth (Neodymium and Samarium Cobalt, Neodymium Iron Boron alloys), magnet disk with the same size as agar block; 10—plate for magnet or agar block; 12—lid covers upper part of frame 1 and forming flow chamber, 8—channels for input and output of liquid containing magnetic particles with antigens.

The principal scheme of magnet works is presented on the bottom of FIG. 10: magnetic and non-magnetic particles are easily separated in the magnetic field. Non-magnetic particles flow out the camber, while magnetic particles with antigens are collected in micro-channels. The methods of antigens detection and/or identification are the same as for cells trapped by filtration discussed above.

EXAMPLE 1

Detection of Microbial Contamination in Liquid Samples

Many different liquid samples in food or pharmaceutical industry must be tested for the presence of bacteria or fungi.

Figure 4:
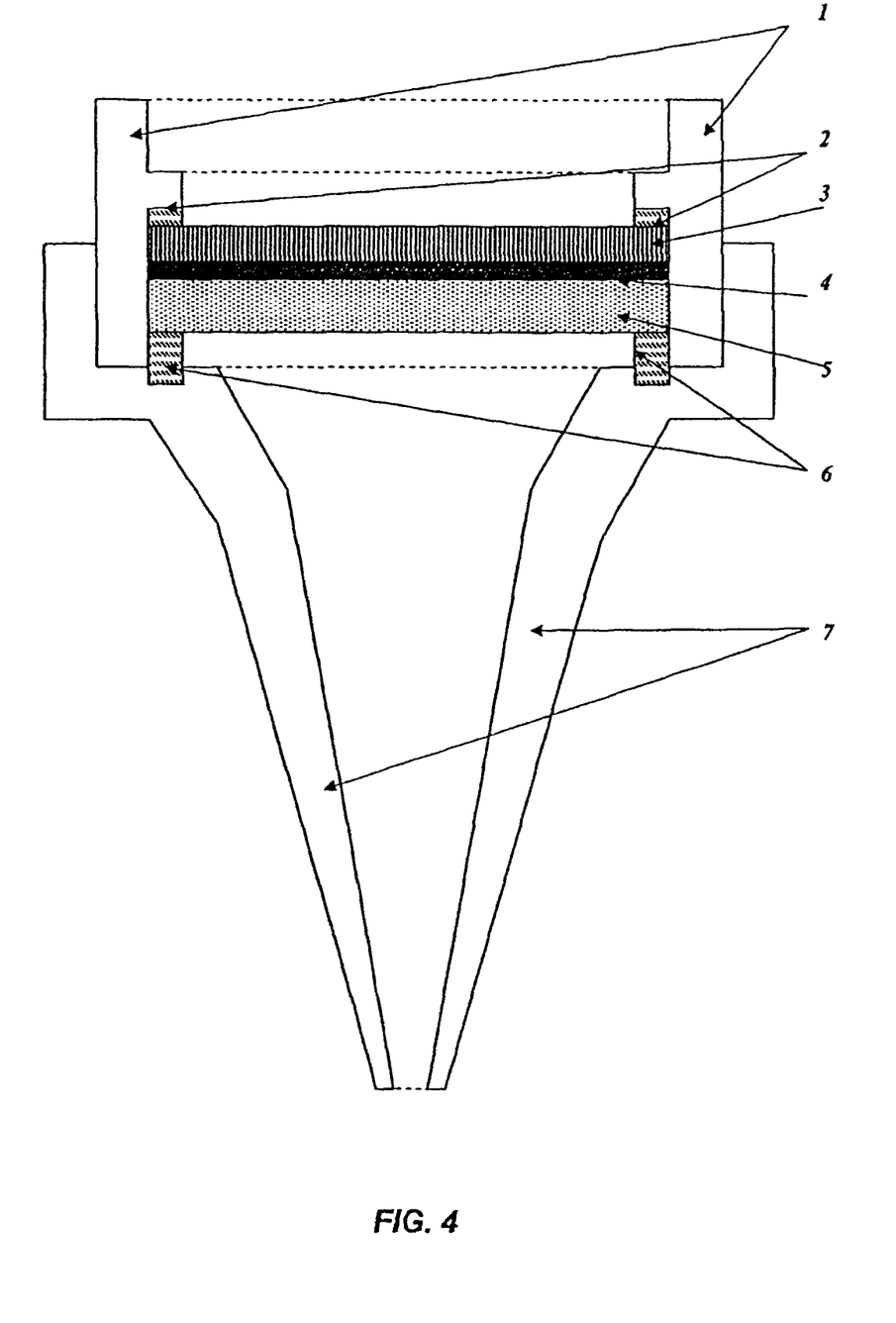
FIG. 4. This drawing shows inner structure of the assembled device for sampling by filtration and placing cells present in a sample in micro channels on the surface of filtration material.
Figure 6:
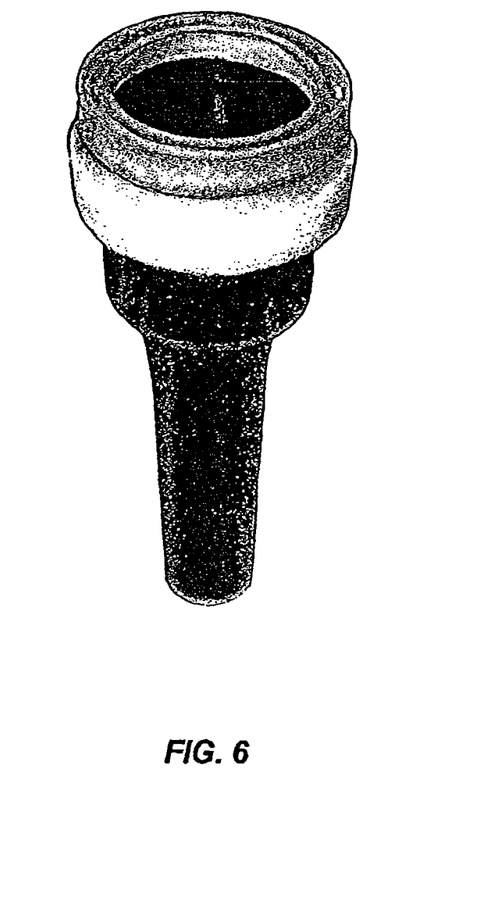
FIG. 6. Demonstrates the real working model of the device shown on FIG. 4 and FIG. 5.

Approximately 100 ml of liquid sample, presumably containing microbes, is filtrated through the device shown in FIGS. 4, 5 and 6. The liquid is easily passed tough a black filter (size of pores is 0.2 microns, cellulosic or nitroellulosic) but cells are trapped at the bottom of the channels on the surface of the filter. After this device is untwisted and a porous disk is removed and substituted by an agar disk preliminarily filled with 4-Methylumbelliferyl phosphate and 4-Methylumbelliferyl acetate (0.1 ml of each with concentration 0.5 mg/ml). The mixture of these fluorogenic substrates guarantees that all live cells will be found because both substrates correspond to big groups of enzymes present in all live cells—Esterases and Phosphatases. Liquid from the agar block containing molecules of named fluorogenic substrates fills all micro-channels in several seconds. The device (with microbial cells in: some of the channels) is placed in an incubator (temperature 40-45° Celsius) for 20-30 minutes. After incubation the device is placed under a fluorescent microscope with excitation light around 300-380 nm and fluorescence around 420-480 nm. The micro-channels containing live cells can be easily differentiated by bright blue fluorescence in comparison with dark "empty" micro-channels. Even one single live cell in 100 ml can be reliably found in 30-40 minutes instead of 3-5 days by a conventional method of growth on Petri plates.

EXAMPLE 2

Identification of *Escherichia coli* O:157 in Samples

A 100 ml sample of liquid is filtrated through the device using a white nitrocellulose filter and colorless micro-channel plate. About 2 ml of standard conjugated antibody for *E. coli* O:157 antigens with Horseradish Peroxidase (HRP) are added to the device and slowly—part by part, in several minutes—filtrated through the device; the conjugate (Ab+HRP) is attached to the surface of *E. coli* O:157 if the cells are present in some of the channels; After that, 50 ml of distilled water is filtrated through the device in order to wash out the rest of the conjugate. An agar block containing: solution of 3,3',5,5'-Tetramethylbenzidine is added to the device instead of porous holder for filter. Incubation is for 35-40 minutes at 40° C. After incubation, the device with filter is placed under a light microscope (multiptication=X100). Micro-channels containing *E. coli* O:157 appear as blue dots. Other micro-channels appear as white dots. Even one cell in 100 ml could be found in less than one hour using this method and device. The regular procedure needs a preliminary growth period of at least 24-48 hours on Petri plates. Flow cytometry allows a microbiologist to find one cell colored by antibody+fluorochrom, practically immediately after it passes a laser beam in the detection zone; however, it needs many hours to pass 100 ml of sample through a 10 micron nozzle of detection zone. The price of Flow cytometers is around $ 100,000. PCR reaches the same results in about 3-4 hours and involves a complicated and expensive technique. In addition, the reliability of PCR analysis in mixtures of different species is not good enough.

EXAMPLE 3

Detection and Identification by Coated Magnetic Particles

Detection and identification of bacteria, viruses, and biomolecules in a sample with the help of magnetic particles consists of several stages. First stage: addition of magnetic particles coated by antibody to the sample presumably containing detected organisms or biomolecules. In this stage, the object is attached to the magnetic particle by Ab-Ag interaction. Second stage: liquid containing magnetic particles together with mixture of other particles passes through the device (FIG. 10). Magnetic particles are separated in micro-channels by magnetic field, and other particles flow out through output channel. Third stage antibody-enzyme conjugate passes through array of micro-channels and is attached to antigens trapped on magnet particles: bacteria, viruses, or biomolecules. Fourth stage: substitute magnet with transparent porous holder for filter and wash out the surplus of conjugate by distilled water: Fifth stage: remove porous holder for filter and add agar block containing artificial substrate to enzyme of conjugate. Sixth and seventh stages: incubate the device at 35-45° C. for 15-45 minutes (depends on conjugate and object), and enumerate colored or fluorescent (depends on version) micro-channels. Color or fluorescence in some micro-channels indicates presence of object attached to magnetic particle in the first stage. This procedure is generally common for all biological objects, such as cells, viruses, and biomolecules. Some objects can have such a small number of antigenic sites that attached enzymes (indicator molecules) are not able to reach a detectable concentration under a microscope (light or fluorescent). This drawback can be improved by use of smaller micro-channels and/or implementation of a more sophisticated source of excitation light (mini UV lasers) and photomultiplier (image intensifier) instead of visual detection.

What is claimed is:

1. An apparatus for detecting, identifying, or enumerating a microorganism or particle with attached biomolecule, microorganism or virus, the apparatus comprising:
    a micro-channel plate having a top surface and a bottom surface with a plurality of micro-channels formed therein extending from said top surface to said bottom surface of the micro-channel plate, the micro-channels having an opening in said top surface extending to said bottom surface of the micro-channel plate, for detecting in a filtered sample without preliminary growth the microorganism or particle with attached biomolecule, microorganism or virus in the plurality of micro-channels, said micro-channel plate fabricated from a single disc having a diameter of at least 25 mm, said plurality of micro-channels ranging in number between 100,000 to 1,000,000 micro-channels per square centimeter of the micro-channel plate and spaced about 1 μm to 2 μm apart so that the micro-channel plate contains at least about 25,000,000 micro-channels;
    a filter having a top surface and a bottom surface, said top surface positioned adjacent to said bottom surface of said micro-channel plate for filtering the microorganism or particle with attached biomolecule, microorganism or virus;
    a removable porous filter holder having a top surface and a bottom surface, said top surface positioned adjacent to said bottom surface of said filter; and
    an agarose block containing artificial substrate having a top surface and a bottom surface, said agarose block being a replacement for said filter holder such that following completion of the filtering of the microorganism or particle with attached biomolecule, microorganism or virus, said filter holder is removed and said top surface of said agarose block is positioned adjacent to said bottom surface of said filter,
    wherein the plurality of micro-channels are substantially filled by the artificial substrate from said agarose block resulting in said microorganism or particle appearing as a visible colored or fluorescent dot.

2. The apparatus according to claim 1, wherein the micro-channel plate is colorless and the filter is colorless or white to allow light to pass from a light microscope through the micro-channel plate to make more visible said colored or fluorescent dot.

3. The apparatus according to claim 1, wherein the micro-channel plate and the filter are black to limit background fluorescence when a fluorescent microscope is used for detection of said fluorescent dot.

4. The apparatus according to claim 1, further comprising:
a magnetic field device for depositing magnetic particle(s) coated with antibodies specific for biomolecule(s), microorganism(s), or virus(es), or antigens that are attracted to the antibodies through antibody-antigen interaction.

5. The apparatus according to claim 1, wherein the micro-channel plate has an angle between the micro-channels and the surface of a micro-channel glass plate of approximately 90°.

6. The apparatus according to claim 1,-wherein the artificial substrate for detecting, identifying or enumerating the microorganism or particle with attached biomolecule, microorganism or virus is selected from the group consisting of 2-nitrophenol, 4-nitrophenol, 5-bromo-4-chloro-3-indoxol, 3-indoxol, 5-bromo-6-chloro-3-indoxol, 6-chloro-3-indoxol, 5-iodo-3-indoxol, N-methylindoxol, 3,3',5,5'-tetramethyl-benzidine dihydroxchloride, tetrazolium salts, 4-methylumbelliferone, 7-amido-4-methylcoumarin, fluorescein, eosine, glycosidases, esterases, phosphatases, peptidases, sulfatases and dehyrogenases.

7. The apparatus according to claim 1, wherein the plurality of micro-channels are filled with said artificial substrate via capillary force.

8. The apparatus according to claim 1, wherein each of the plurality of micro-channels has a length of approximately 100 µm or less.

9. The apparatus according to claim 1, wherein each of the plurality of micro-channels has a volume of approximately 300,000 µm$^3$ or less.

10. The apparatus according to claim 1, wherein one microorganism in each of said plurality of micro-channels provides a corresponding concentration of millions of cells per milliliter of sample.

11. The apparatus according to claim 1, further comprising:
a plurality of particles coated with an antibody to which biomolecule(s), microorganism(s), or virus(es) are specifically attached, wherein each of the particles together with the attached biomolecule(s), microorganism(s), or virus(es) are sufficiently large to be captured by the filter, and wherein each of the biomolecule, microorganism, or virus without the attached particle is not sufficiently large to be captured.

12. The apparatus according to claim 1, further comprising:
a lid having micro-channels formed therein coupled to the micro-channel plate to form a flow chamber, the lid having an input and output to transport liquid containing a magnetic particle with attached biomolecule, microorganism, or virus; and
a magnet for separating the magnetic particle from non-magnetic particles and depositing the magnetic particles into the plurality of micro-channels, wherein the magnet containing a magnetic field is substituted for the agarose block containing artificial substrate.

13. A method of detecting, identifying, or enumerating microorganism(s), or particle(s) with attached biomolecule(s), microorganism(s), or virus(es), the method comprising the steps of:
providing the apparatus as recited in claim 1;
providing a filtrating material;
filtering a sample through the filtrating material thereby trapping microorganism(s), or particle(s) with attached biomolecule(s), microorganism(s), or virus(es) in the micro-channels;
providing an indicator to the micro-channels that rapidly reacts with the microorganism(s) or the particle(s) with attached biomolecule(s), microorganism(s), or virus(es) thereby creating a detectable concentration in the micro-channel for as few as one microorganism or one particle with attached biomolecule(s), microorganism(s), or virus(es).

14. The method according to claim 13, further comprising the step of:
introducing liquid into the microchannels via capillary force.

15. The method according to claim 13, further comprising the step of:
detecting, identifying, or enumerating: i) dangerous or pathogenic microorganisms for medical diagnostics of human or veterinary medicine; ii) microbes for industrial microbiology; iii) contaminants of air, water, and soil, for environmental analysis; and/or iv) contagious or pathogenic microorganisms for epidemiology or biodefense.

16. The method according to claim 13, wherein the indicator is one or more biochemical indicator reagent(s) selected from the group consisting of
fluorogenic or chromogenic substrates;
special enzymes and artificial substrate(s);
enzyme immunoassays; and
a conjugate with an artificial substrate.

17. The method according to claim 13, further comprising the step of:
enumerating micro-channel(s) having an appearance of colored or fluorescent dots to determine a concentration of microorganism(s) in a sample based on the results of the enumeration step and on the volume of the sample.

18. The method according to claim 13, wherein the indicator is confined to a micro volume thereby maintaining a concentration level of indicator substance sufficient to provide detection.

19. The method according to claim 13, further comprising the steps of:
adding to the sample, magnetic particle(s) coated with an antibody for a microorganism, biomolecule, or virus that is sought;
trapping the magnetic particle(s) in micro-channels by a magnetic field; and
identifying, enumerating, or detecting a microorganism by enzyme or enzyme immunoassay or identifying, enumerating, or detecting a biomolecule by enzyme immunoassay.

20. A method for of detecting, identifying, or enumerating microorganism(s) or particle(s) with attached biomolecule(s), microorganism(s), or virus(es), the method comprising the steps of:
providing the apparatus as recited in claim 1, wherein the plurality of micro-channels are open on both ends;
trapping as few as one microorganism, or one particle with attached biomolecule(s), microorganism(s) or virus(es) in at least one of the plurality of micro-channels; and providing a fluid that will fill the plurality of micro-channels via capillary action.

21. A method of detecting, identifying, or enumerating microorganism(s) or particle(s) coated with biomolecule(s), microorganism(s), or virus(es), the method comprising the steps of:
provi­ding the apparatus as recited in claim 1;
providing a sample to be tested in the device with the plurality of micro-channels; and
changing a corresponding concentration within a micro-channel from zero cells per milliliter to at least five orders of magnitude of cells per milliliter by trapping as few as one cell in the micro-channel.

* * * * *